United States Patent [19]

Chang

[11] Patent Number: 5,274,075
[45] Date of Patent: Dec. 28, 1993

[54] NEWLY IDENTIFIED HUMAN EPSILON IMMUNOGLOBULIN PEPTIDES AND RELATED PRODUCTS

[75] Inventor: Tse W. Chang, Houston, Tex.

[73] Assignee: Tanox Biosystems, Inc., Houston, Tex.

[21] Appl. No.: 515,604

[22] Filed: Apr. 27, 1990

Related U.S. Application Data

[63] Continuation-in-part of Ser. No. 468,766, Jan. 23, 1990, which is a continuation-in-part of Ser. No. 369,625, Jun. 21, 1989, which is a continuation-in-part of Ser. No. 272,243, Nov. 16, 1988, Pat. No. 5,091,313, which is a continuation-in-part of Ser. No. 229,178, Aug. 5, 1988, abandoned, which is a continuation-in-part of Ser. No. 226,421, Jul. 29, 1988, which is a continuation-in-part of Ser. No. 140,036, Dec. 31, 1987, abandoned.

[51] Int. Cl.$^5$ .................. C07K 7/10; C07K 15/00
[52] U.S. Cl. .................. 530/324; 530/387.1; 530/387.9
[58] Field of Search ............... 530/388, 324, 387, 324, 530/387.1, 387.9

[56] References Cited

PUBLICATIONS

Ishida, N. et al., *EMBO Journal*, vol. 1(19): 1117–1123, 1982.
Ishida et al., The EMBO J. vol. 1 1117–23 (1982).
Word et al. "The Murine Immunoglobulin & Gene Expresses Multiple Transcripts from a unique membrane exon " (particularly; p. 895, 2nd column) EMBO Journal 2:887–898 (1983).

*Primary Examiner*—Lester L. Lee
*Assistant Examiner*—Susan Perkins
*Attorney, Agent, or Firm*—Eric P. Mirabel; Giulio A. DeConti, Jr.

[57] ABSTRACT

The invention includes human ε chain transmembrane anchor peptide resulting from mRNA splicing other than the Cε4 exon, the εm1 exon, and the εm2 exon. Two new peptides in particular have been specifically identified. These novel peptides are not present in the conventional secreted (and circulating) IgE. These peptides provide antigenic sites for antibody binding. Thus, the invention further includes antibodies to such peptide segments, as well as such antibodies conjugated to cytotoxic agents, and their use in extracorporeal or in vivo therapy.

4 Claims, 4 Drawing Sheets

```
···CH4 domain··· GTG·TCT·GTA·AAT·CCC·GAG·CTG·GAC·    |← em1 exon (122 N)
                  V   S   V   N   P   E   L   D GTG·TGC·GTG·GAG·GAG·GCC·GAG·GGC·GAG·GCG·CCG·TGG·
 V   C   V   E   E   A   E   G   E   A   P   W ACG·TGG·ACC·GGC·CTC·TGC·ATC·TTC·GCC·GCA·CTC·TTC·
 T   W   T   G   L   C   I   F   A   A   L   F CTG·CTC·AGC·GTG·AGC·TAC·AGC·GCC·GCC·CTC·ACG·CTC·
 L   L   S   V   S   Y   S   A   A   L   T   L ↓ em2 exon (84 N)
CTC·ATG·GTG·CAG·CGG·TTC·CTC·TCA·GCC·ACG·CGG·CAG·
 L   M   V   Q   R   F   L   S   A   T   R   Q GGG·AGG·CCC·CAG·ACC·TCC·CTC·GAC·TAC·ACC·AAC·GTC·
 G   R   P   Q   T   S   L   D   Y   T   N   V

CTC·CAG·CCC·CAC·GCC·TAG·
 L   Q   P   H   A   ***
```

Figure 2A

```
                                                          em0 exon (156 N)
···CH4 domain···GTG·TCT·GTA·AAT·CCC·GGG·CTG·GCT·
                 V   S   V   N   P   G   L   A GGC·GGC·TCC·GCG·CAG·TCC·CAG·AGG·GCC·CCG·GAT·AGG·
 G   G   S   A   Q   S   Q   R   A   P   D   R GTG·CTC·TGC·CAC·TCC·GGA·CAG·CAG·CAG·GGA·CTG·CCG·
 V   L   C   H   S   G   Q   Q   Q   G   L   P AGA·GCA·GCA·GGA·GGC·TCT·GTC·CCC·CAC·CCC·CGC·TGC·
 R   A   A   G   G   S   V   P   H   P   R   C CAC·TGT·GGA·GCC·GGG·AGG·GCT·GAC·TGG·CCA·GGT·CCC·
 H   C   G   A   G   R   A   D   W   P   G   P em1 exon (122 N)
CCA·GAG·CTG·GAC·GTG·TGC·GTG·GAG·GAG·GCC·GAG·GGC·
 P   E   L   D   V   C   V   E   E   A   E   G GAG·GCG·CCG·TGG·ACG·TGG·ACC·GGC·CTC·TGC·ATC·TTC·
 E   A   P   W   T   W   T   G   L   C   I   F GCC·GCA·CTC·TTC·CTG·CTC·AGC·GTG·AGC·TAC·AGC·GCC·
 A   A   L   F   L   L   S   V   S   Y   S   A em2 exon (84 N)
GCC·CTC·ACG·CTC·CTC·ATG·GTG·CAG·CGG·TTC·CTC·TCA·
 A   L   T   L   L   M   V   Q   R   F   L   S GCC·ACG·CGG·CAG·GGG·AGG·CCC·CAG·ACC·TCC·CTC·GAC·
 A   T   R   Q   G   R   P   Q   T   S   L   D TAC·ACC·AAC·GTC·CTC·CAG·CCC·CAC·GCC·TAG·
 Y   T   N   V   L   Q   P   H   A  ***
```

Figure 2B

```
                                                          εm2' exon (137 N)
···CH4 domain···GTG·TCT·GTA·AAT·CCC·GGT·GCA·GCG·
                 V   S   V   N   P   G   A   A GTT·CCT·CTC·AGC·CAC·GCG·GCA·GGG·GAG·GCC·CCA·GAC·
 V   P   L   S   H   A   A   G   E   A   P   D CTC·CCT·CGA·CTA·CAC·CAA·CGT·CCT·CCA·GCC·CCA·CGC·
 L   P   R   L   H   Q   R   P   P   A   P   R CTA·GGC·CGC·GGG·CAC·TCA·CGC·TCC·ACC·AGG·CCC·AGC·
 L   G   R   G   H   S   R   S   T   R   P   S

TTT·TTC·TCT·GCC·AGC·GCC·TGA·
 F   F   S   A   S   A   ***
```

Figure 2C

NEWLY IDENTIFIED HUMAN EPSILON IMMUNOGLOBULIN PEPTIDES AND RELATED PRODUCTS

RELATED APPLICATIONS

This application is a continuation-in-part of U.S. patent application Ser. No. 07/468,766, filed Jan. 23, now pending 1990, which is a continuation-in-part of U.S. patent application Ser. No. 07/369,625filed Jun. 21, now pending 1989 which is a continuation-in-part of U.S. patent application Ser. No. 07/272,243, filed Nov. 16, 1988, now U.S. Pat. No. 5,091,313 which is a continuation-in-part of U.S. patent application Ser. No. 07/229,178, filed Aug. 5, 1988, now abandoned which is a continuation-in-part of U.S. patent application Ser. No. 07/226,421, now pending, filed Jul. 29, 1988, which is a continuation-in-part of U.S. patent application Ser. No. 07/140,036, filed Dec. 31, 1987, now abandoned.

FIELD OF THE INVENTION

The invention relates to newly identified human ε immunoglobulin peptide segments, which include the transmembrane anchor peptide segment of the ε chain, and antibodies and related products.

BACKGROUND OF THE INVENTION

The immediate-type hypersensitivity, such as extrinsic asthma, hay fever, and allergic responses to certain foods or drugs, is mediated primarily by one isotype of the immunoglobulins, IgE. In an IgE-mediated allergic response, the allergen binds to IgE which are bound to receptors on the surface of mast cells and basophilic leukocytes (basophils). The binding of the allergen causes crosslinking of the surface IgE molecules and hence the underlying receptors for the Fc portion of IgE (FcεR), thereby triggering the release of pharmacologic mediators such as histamine, the slow-reacting substance of anaphylaxis (SRA), and serotonin. The release of these mast cell and basophil products causes the pathological reactions and symptoms of allergy.

IgE is produced by a particular class of B cells, the surface IgE-bearing B lymphocytes. In individuals sensitized to specific allergens, the allergen-specific IgE is produced by these B cells continuously. Recently, Whitaker (U.S. Pat. No. 4,714,759) described a method of treating allergy patients with toxin-conjugated antibodies that were specific for IgE. The intended effect of the immunotoxin is to kill IgE-producing B cells.

In the first related U.S. patent application Ser. No. 07/140,036, filed Dec. 31, 1987, and in its continuation-in-part application Ser. No. 07/140,036, filed Jul. 29, 1988, it is noted that IgE binds to the FcεR receptors of IgE on the surface of basophils and mast cells very strongly. The association constant, Ka, is about $1 \times 10^{10}$ liter/mole. Even though IgE is not synthesized by basophils and mast cells, the very strong and stable association of IgE with FcεR means that IgE is virtually always present and exposed on the surface of these cells. The related applications indicate that an immunotherapeutic agent targeting the IgE on B cells must not react with the IgE on basophils and mast cells, in order to avoid triggering an allergic reaction. Antibodies which react with IgE will cross-link IgE and the underlying FcεR on basophils and mast cells and, when administered in vivo, will induce systemic histamine release leading to anaphylaxis.

In the related patent applications the development of monoclonal antibodies that recognize an antigenic epitope present on the IgE which is expressed on B cells, but not the IgE on basophils and mast cells, is described. In addition, the method of using these antibodies or toxin-conjugates of these antibodies for treating allergy is described. The unconjugated antibody, by causing antibody-dependent cellular cytotoxicity (ADCC) and complement-mediated cytolysis and the toxin-conjugated antibodies can directly cause cytolysis of the IgE-expressing B cells. Both of these mechanisms can lead to the depletion of IgE-producing B cells without causing cross-linking of the IgE bound on the basophils and mast cells. The IgE epitopes present on B cells but absent on basophils and mast cells are termed ige.bl epitopes (bl denoting B lymphocytes).

Immunoglobulins consist of two peptide chains, a heavy chain and a light chain. In IgE, the heavy chain is designated as the ε chain. The parent application, U.S. application Ser. No. 07/468,766, describes that the IgE, and other immunoglobulins, which are bound to B cells are different from secreted IgE and other secreted immunoglobulins in that the bound form includes an extra peptide segment on the heavy chain which anchors the immunoglobulin to the B cell membrane. These peptide segments span through the B cell plasma membrane. The known DNA sequences of the gene segments encoding the cell-bound forms of immunoglobulins, including mouse and rat IgE, and in human IgM and IgD, indicate that the transmembrane anchor peptide includes three distinct portions: a middle hydrophobic portion which is embedded in the cell membrane lipid bilayer, a C-terminal hydrophilic portion located on the cytoplasmic side of the membrane, and an N-terminal portion located on the extracellular side of the membrane.

The parent application also describes the nucleotide sequence of the genomic DNA segments encoding the transmembrane anchor peptide of human ε chain. Two exons encoding the transmembrane anchor peptide of the human ε chain were identified. The first membrane exon (εm1 exon), having 122 bp, is located about 1.5K bp from the exon for the CH4 domain. See FIGS. 1 and 2A. The second membrane exon (εm2 exon), having 84 bp including the termination codon TGA, is separated from the εm1 exon by 82 bp. See FIGS. 1 and 2A.

This evidence discussed in detail in the parent application indicates that a 15 amino acid peptide segment toward the N-terminus of the transmembrane anchor peptide in human ε chain, designated as the migis-ε peptide, is the extracellular portion of the human ε transmembrane anchor peptide. Because it is normally located outside the B cell, the migis-ε peptide can form entirely or in-part an epitope and antibodies which are specific to this epitope can be generated. These antibodies can be used for causing the lysis of B cells expressing membrane-bound IgE.

SUMMARY OF THE INVENTION

The invention includes an ε immunoglobulin transmembrane anchor peptide resulting from a mRNA splicing other than the splicing of the Cε4 exon, the εm1 exon, and the εm2 exon. These E chain peptides contain peptide segments which are not present in the conventional membrane-bound or secreted IgE. These peptide segments provide antigenic sites for antibody binding. Thus, the invention further includes antibodies to such peptide segments, as well as such antibodies conjugated to cytotoxic agents, and their use in in vivo or extracorporeal therapy.

mRNA species encoding two new human ε chains peptides been identified. Their sequences are derived from the splicing of: (1) the Cε4 exon, the εm1' exon (consisting of the εm1 segment plus a contiguous 156 bp segment of the εm0 segment), and the εm2 exon; (2) the Cε4 exon and the εm2' exon (having 137 bp including the TGA termination codon and consisting of the entire εm2 segment plus an additional contiguous segment, but shifted from the reading frame of the εm2 codon). These peptide segments, as well as others corresponding to other cDNA sequences of the human ε chain gene, can be used as noted above.

The advantage in therapy of these antibodies over those that bind epitopes common to IgE in both bound and secreted form is that the latter will form an immune complex of antibody-IgE. The immune complex may create problems with kidney or other physiological functions.

These novel peptide segments, or anti-idiotypic antibodies to antibodies to these peptide segments, have a number of uses described in detail below. They can also be used for assaying serum for antibody reactive with such peptides or anti-idiotypes. This would be useful following therapeutic administration of such antibody to an individual. A strongly positive assay would indicate that such antibody was still present in the individual and that no further antibody need be administered, whereas a negative or low titre would indicate the opposite.

The antibodies themselves could also be used in the analyses of allergic sensitivity. These antibodies could be used in assaying for IgE bearing the novel peptides in serum or on leukocytes.

BRIEF DESCRIPTION OF THE DRAWINGS

FIG. 2A shows DNA segment encoding the peptide sequence of the human ε chain transmembrane anchor peptides resulting from the linkage shown uppermost in FIG. 1, wherein the Cε4 exon (of the CD4 domain) is linked to the εm1 exon, which is linked to the εm2 exon.

FIG. 2B shows the DNA segment encoding the peptide sequence of the human ε chain transmembrane anchor peptides resulting from the linkage shown in the middle of FIG. 1, wherein the Cε4 exon is linked to the εm1' exon, which is linked to the εm2 exon.

FIG. 2C shows the DNA segment encoding the peptide sequence of the human ε chain transmembrane anchor peptides resulting from the linkage shown lowermost in FIG. 1, wherein the Cε4 exon is linked to the εm2' exon.

Figure 1:
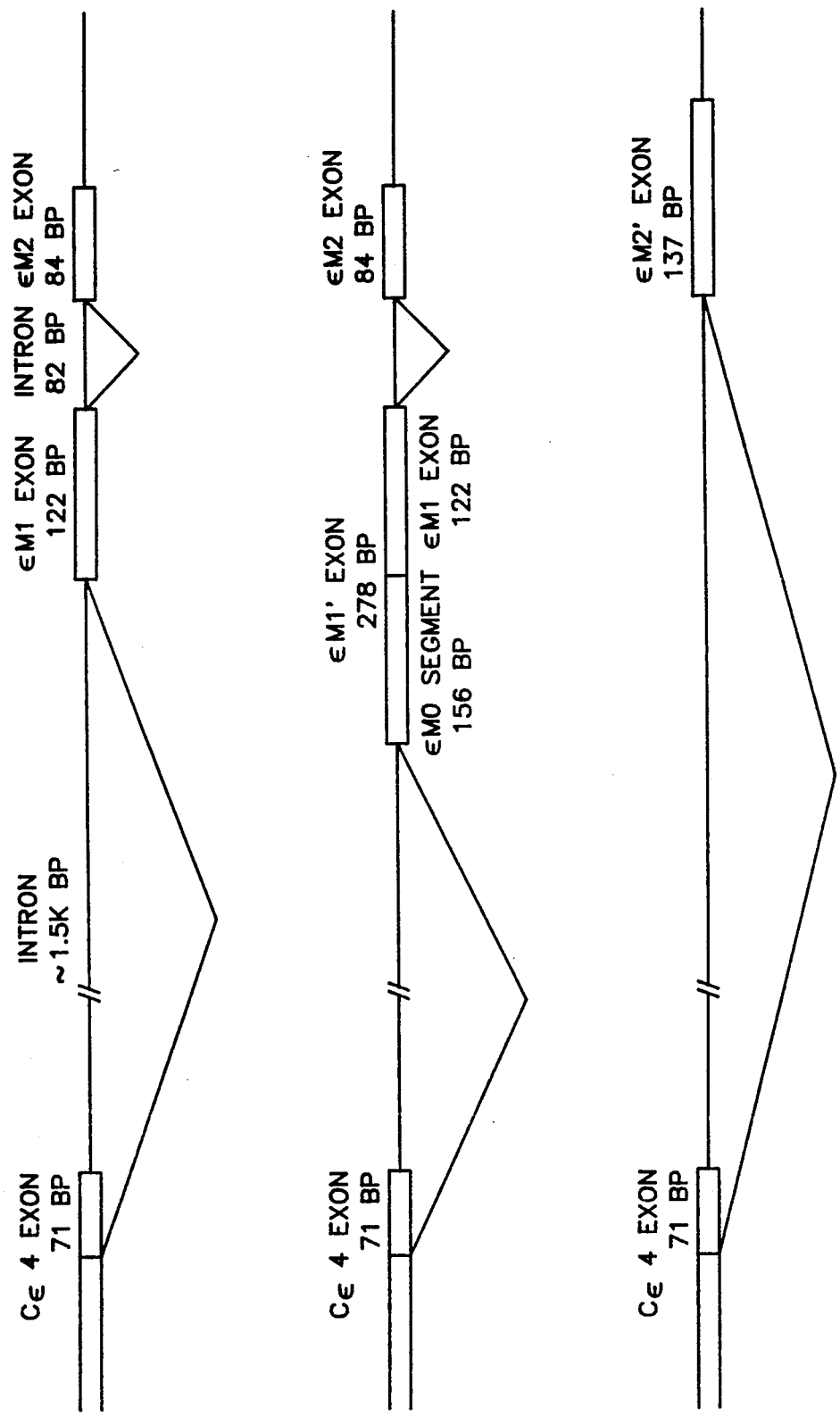
FIG. 1 shows MRNA which create three different human ε immunoglobulin peptides, the uppermost linking having been previously disclosed in U.S. application Ser. No. 07/468,766.

DETAILED DESCRIPTION OF THE PREFERRED EMBODIMENTS AND THEIR MANNER AND PROCESS OF MAKING AND USING

The invention describes the discovery of novel human ε chains resulting from a mRNA splicing other than the the splicing of the Cε4 exon, the εm1 exon, and the εm2 exon. An example of identifying the MRNA encoding the two novel peptides of the invention, using polymerase chain reaction (PCR) techniques, is set forth below.

The parent application, U.S. Ser. No. 07/468,766, describes in detail how to determine the nucleotide and amino acid sequences of the antigenic epitopes located on the extracellular segment of the membrane-bound region of the human ε chain. These epitopes are designated as the ε.mb/ec epitopes. Several approaches are possible, including starting with a MRNA preparation of a human myeloma cell line which expresses IgE on the surface. The mRNA can be used in establishing a cDNA library which is then screened with DNA probes for the transmembrane region gene segment of ε chain region.

An alternative approach, also described in detail in U.S. Ser. No. 07/468,766, is to use PCR technology to successively amplify and purify the DNA sequence of the ε transmembrane region. The DNA is then sequenced.

Another alternative approach described in U.S. Ser. No. 07/468,766 is to screen the human genomic library. The gene segment corresponding to the membrane bound region can be determined with a probe prepared from the homologous mouse gene of the transmembrane segment, and the sequence of this segment is then determined.

In the present invention, the nucleotide sequencing was performed on the cDNA derived from MRNA isolated from human cells expressing membrane-bound IgE. A commercially available human IgE expressing myeloma, SKO-007 (from ATCC), was used.

The DNA segments of cDNA regarded as pertinent to identification and characterization of the transmembrane regions of human E chain were amplified by PCR, as described further below, using oligonucleotide primers having sequences corresponding to segments in CH4 and in regions of the membrane exons. The nucleotide sequencing of the various cDNA clones revealed two alternative splicings in the membrane exon region of human ε chain gene, in addition to the one previously described in U.S. Ser. No. 07/468,766.

All three splicings are depicted in FIG. 1, and in FIGS. 2A, 2B, and 2C. The uppermost splicing shown in FIG. 1, and in FIG. 2A, is that previously described in U.S. application Ser. No. 07/468,766, and has the structure corresponding to that wherein the Cε4 exon is linked to the εm1 exon which is linked to the εm2 exon. The start and finish of the εm1 and εm2 exons are more clearly seen in FIG. 2A.

A first new splicing is shown in the middle of FIG. 1 and in FIG. 2B, and has the structure corresponding to that wherein the Cε4 exon is linked to the εm1' exon, which is linked to the εm2 exon. The εm1' exon includes the εm1 segment and a new 156 bp segment designated εmo. The εmo segment is more clearly seen in FIG. 2B. The corresponding first novel εmo peptide of the invention is shown in bold face type.

A second new splicing is shown lowermost in FIG. 1 and in FIG. 2C, and has the structure corresponding to that wherein the Cε4 exon is linked to the εm2' exon. The εm2' exon is one bp frame shifted from the εm2 exon, and can be more clearly seen in FIG. 2C. The corresponding second novel εm2' peptide is shown in bold face type.

The εmo peptide is likely to be more immunogenic than the εm2' peptide, because the εm1 peptide has a more clearly hydrophobic transmembrane region of about 25 hydrophobic uncharged amino acid residues. The hydrophilic portion of this peptide will be more likely to be exposed on the B cell surface to provide antigenic sites for antibody binding. Nevertheless, the peptide corresponding to the second new splicing may also be antigenic, as it may be anchored to the cell surface by phosphatidylinositol glycan mechanism.

An example of carrying out PCR and peptide synthesis is set forth below.

EXAMPLE 1

Cloning and nucleotide sequencing of cDNA segment encoding the transmembrane region of human ε immunoglobulin

Methods

Initially, two cell lines that express human E chain on their cell surface were studied. One line, SKO-007, a subclone of U266, was obtained from the ATCC. U266 was a myeloma cell line established from the blood sample of a myeloma patient. The other cell line, SE44, secretes and expresses on the cell surface hu/mu chimeric IgE. SE44 was derived from a mouse myeloma, SP2/0, which was transfected with chimeric genomic DNA (huCε/muV$_H$,huC$_K$/muV$_K$), of which the Cε was derived from germline DNA and the variable regions were derived from those of a mouse hybridoma which secreted monoclonal antibody specific for gp120of the AIDS virus, HIV-1. The construction of the transfectoma was described in the related applications noted above.

Total RNA was extracted in guanidinium thiocyanate from $5 \times 10^7$ SKO-007 or SE-44 cells. The first strand CDNA was synthesized by AMV reverse transcriptase (Life Sciences, Inc., Petersburg, Fla.) according to the procedure described by the manufacturer. The primers used in the preparation of cDNA were the 3' end primers used in the PCR amplification of particular segments of cDNA for examination, cloning, and characterization.

The DNA segments of the CDNA thougt to be pertinent in regards to the identification and characterization of the transmembrane region of human ε chain were amplified by PCR using oligonucleotide primers having sequences representing different regions encoding the transmembrane domain. During the course of the experiements described in this application, four oligonucleotide primers, which were synthesized by a service laboratory in Baylor College of Medicine, Houston, Tex., were used.

The four oligonucleotide primers are
1) 5'CAGAATTCAGATGAGTTCATCTGCCGTGC3' located in CH4 domain;
2) 5'GGAGGGATTCGTTGGTGTAGTCGA3' located in εm2 domain (complementary strand was used);
3) 5'GCGAATTCGATGCAGAGGCCGGTCCACG3' located in εm1 domain (complementary strand was used);
4) 5'CTCGGCAGTCCCTGCTGCTGT3' located in the segment upstream from εm1 exon, referred to as εm0 segment in FIG. 1 (complementary strand was used).

The PCR was carried out in a DNA Thermal Cycler (Perkin Elmer Cetus, Norwalk, Conn.) and the reaction conditions were: denaturing at 94° for 1 min, annealing at 50° for 2 min, and Taq polymerase (US Biochemical, Cleveland, Ohio) reaction at 72° for 45 sec. The reaction cycles were 40.

The products from PCR were fractionated on gel by electrophoresis and the gel fractions containing the major bands or bands with predicted sizes were cut. The DNA was extracted from the gel and ligated into plasmid pUC19 (US Biochemical, Cleveland, Ohio) at the restriction site of Sma 1. The recombinant plasmids containing inserts were identified by restriction enzymes digestion, and amplified and purified using a CIRCLEPREP kit (BIO 101, La Jolla, Cal.). DNA sequences of the inserts were determined by the method of dideoxy sequencing on double stranded DNA.

Results

The nucleotide sequencing of the cDNA segments revealed that the cDNA predicted from the splicing of CH4 domain to εm1 exon and εm1 exon to εm2 exon existed. The sequence of the mRNA and the derived amino acid sequence of the corresponding polypeptide is shown in FIG. 2A.

The nucleotide sequences of other cDNA clones derived from 1 round, 40 cycle PCR revealed results that two alternative splicing in the regions of the membrane exons of human ε gene, which were not reported before, occured.

One alternative splicing results from the splicing of CH4 domain at the same expected donor site to an acceptor site 156 bp upstream of the εm1 exon. This alternative splicing results in mRNA that contains both εm1 segment and εm2 exon in the same reading frame as the conventional mRNA. The first exon, referred to as εm1' exon, is now 278 bp long, being composed of εm0 segment (156 bp) and εm1 segment (122 bp). The translated ε peptide would have extra 53 amino acid residues as indicated by the bold-faced single-letter amino acid designation in FIG. 2B.

The other alternative splicing links the CH4 domain at the expected splicing donor site directly to εm2 domain, leaving out εm1 domain. The reading frame of εm2 is shifted and encodes for a peptide of different sequence and different length from one encoded by the original εm2 exon. This new exon (referred to as εm2) has 137 bp (including TGA termination codon) and encodes for 45 amino acid residues (the boldfaced peptide segment in FIG. 2C). This peptide segment does not have a clear transmembrane segment, which is usually characterized by a stretch of 25 hydrophobic or noncharged amino acid residues.

B. Peptide Synthesis

As described more fully below, the novel human e chain peptides can be used to elicit antibodies which react specifically with the novel forms of immunoglobulin E. For this purpose, the peptides can be chemically synthesized by standard techniques of peptide synthesis. A preferred method for synthesizing the peptides is with RaMP system (DuPont, Wilmington, Del.), which applies Fmoc chemistry. Alternatively, the proteins can be biosynthesized by expressing the DNA segments encoding the peptides.

As immunogens, whole IgE molecules or full lengths of ε chains in the native form described above may be used. Peptides comprising the novel peptide segments and the connecting four amino acids in the CH$_4$domain can also be used. In addition, modified peptides having substantial immunological equivalency can be used. For example, the novel peptide amino acid sequences described above and shown in the FIGURES (middle and lowermost on FIG. 1, FIG. 2B and 2C) can be modified by deletion, insertion or substitution of one or more amino acids which do not essentially detract from their immunological properties. The peptides can also be used as polymers where the amino acid sequence shown above, or equivalent sequence, is the polymer repeat unit.

3. Developing Antibodies to the Novel Peptides

The novel peptides can be used in the immunization of animals to prepare polyclonal and monoclonal antibodies. They can also be used to screen for specific monoclonal antibodies or to characterize specific polyclonal antibodies. They can also be used to purify monoclonal and polyclonal antibodies.

In the process of preparing for monoclonal antibodies specific for these peptides, it is not necessary to use the novel peptides in both immunization and antibody identification. For example, in immunizing mice for preparing immune spleen cells for fusion with myeloma cells, the immunogen may be the membrane-bound IgE isolated from plasma membrane of IgE-bearing myeloma cells, such as SK007 cells. The immunogen may also be the IgE-bearing myeloma cells.

If using the novel synthetic peptides for immunogens, it is more effective to conjugate them to a protein carrier. A preferred protein carrier is keyhole lympit hemocyanin (KLH). If the peptidic segment lacks a Lys residue or if the Lys residue is in the middle part of the segment, it is desirable to add a Lys residue at the C-terminal end. Because the N-terminus already has an α-amino group, the modified synthetic peptidic will have two amino groups for linking.

Multiple molecules of peptides can be conjugated to each molecule of the carrier protein. With KLH, a preferred molar ratio for peptide/KLH is 10. The method of conjugation is very well established. Cross-linkers such as glutaldehyde or bis (sulfosuccinimidyl) suberate or disulfosuccinimidyl tartarate (Catalogue #21579, 20591, Pierce Chemical Co., Rockford, Ill.) have been used. A preferred cross-linker is the latter.

The immunogen, such as the KLH conjugate, can be used to immunize rabbits, goats, rats, or mice to prepare polyclonal antibodies specific for the novel peptides. Lymphocytes from the spleen or lymph nodes of immune mice and rats can also be taken to prepare hybridomas secreting monoclonal antibodies specific for the novel peptides. A preferred protocol to prepare the monoclonal antibodies is to fuse immune spleen cells of mice with non-secreting mouse myeloma cells, such as NS-1 or SP2/0 cells using polyethylene glycol.

For optimal immunization of mice, 50 μg of the peptide-KLH conjugate in complete Fruend's adjuvant is injected subcutaneously into each mouse for priming. Two and four weeks later, the same amounts of antigen is given s.c. in incomplete Fruend's adjuvant. After about six weeks, the fourth antigen injection is given i.p. in saline. Mice are sacrificed four days after the last injection and the spleens are taken for preparing single cell suspensions for fusion with myeloma cells. Similar protocols can also be used for immunization with purified native human membrane-bound IgE (having attached membrane anchor domain) isolated from the plasma membrane of IgE-bearing human myeloma cells, such as SK007 cells. When human IgE-bearing cells are used as the immunogen, $1 \times 10^7$ cells are injected i.p. at two week intervals.

The fusion procedure with polyethylene glycol and other various procedures concerning cloning and hybridoma culturing have been well established and the preferred protocol is the same as described by Hudson, L. and Hay, F. C. (Practical Immunology, 2nd edition, pp. 303-313, 1980, Blackwell Publishing Co., Boston).

The screening of hybridomas for monoclonal antibodies or the identification of polyclonal antibodies reactive with the novel peptides can be performed with enzyme linked immunosorbent assays (ELISA) using the synthetic peptides as the solid phase antigen. An alternative solid phase antigen is the conjugate of the novel peptides with carrier protein such as bovine serum albumin, different from that used in the immunogen.

Assays described in detail in U.S. application Ser. Nos. 07/226,421, and 07/140,036, the teachings of which are incorporated by reference herein, can be used in further characterization studies. These assays include immunofluorescence staining and histamine release.

4. Experiments with Animal Models

The substances and methods can be on animal model systems, as described in detail in U.S. application Ser. No. 07/468,766. Two relevant animal model systems described there are the Asthma/rhesus monkey model and the mouse model system.

5. Therapy of IgE-mediated Allergy based upon the Selective Elimination of IgE-producing Cells Antibodies specific for the epitopes on the peptides of the invention bind IgE on the surface of IgE-producing B cells and not on basophils and mast cells. The antibodies specific for these epitopes can be used to treat IgE-mediated allergies in humans. The antibodies can be used therapeutically in several ways. The antibodies can be used as effector agents mediating an immune function, as a carrier agents of toxins or cytotoxic drugs, for delivering an effector substance, or as targeting agents for cytotoxic cells, all such uses being as described in U.S. application Ser. No. 07/468,766. The antibodies can be administered systemically or nasally.

For the therapeutic uses in humans, either human or chimeric (or "near-human") IgG antibodies are preferred. Chimeric antibodies comprise a variable or antigen binding (hypervariable or complementarity determining) region derived from an animal antibody and the remaining regions derived from a human antibody. Methods for producing chimeric (e.g. reurine/human) antibodies are well established.

Immunotherapies employing the antibodies of the invention may be used in combination with conventional desensitization immunotherapy. For example, desensitization with allergen may be performed in conjunction with the administration of the antibodies or immunotoxins of the invention to eliminate substantially IgE-producing cells. One major effect of desensitization is the IgG's are induced against the allergen/immunogen. The induction of an IgG response may be most effective when IgE-producing B cells are substantially depleted.

The combination of antibody and desensitization therapy is an attractive form of therapy. IgE-producing B cells may be temporarily depleted (for a few weeks or months) by the antibodies of the invention, but they will eventually repopulate. The combination with desensitization may have longer lasting effects.

B. Immunotherapy Combining an Antibody and a Factor Enhancings, ADCC

Many factors, such as GM-CSF (granulocyte monocyte colony stimulation factor) or M-CSF (monocute colony stimulation factor), are known to induce the proliferation of leukocytes, including those mediating ADCC. The therapeutic effect of the monoclonal antibodies of the invention in treating allergies should be enhanced by combining the use of factors that augment ADCC activities.

C. Immunotoxins Specific for IgE-Producing Cells

Antibodies of the invention can be used with immunotoxin in conjugated form, specifically targeted to IgE-producing B cells. The conjugate binds to IgE-producing B cells, but not to mast cells or basophils. In this way, IgE-producing B cells can be selectively eliminated in a patient suffering from an IgE-mediated allergy.

Conjugates of immunotoxins for selective binding to IgE-producing lymphocytes include cytolytic or cytotoxic agents conjugated to the monoclonal antibodies of the invention. The cytolytic agents can be selected from any of the available substances including ricin, PseudoNonas toxin, diphtheria toxin, pokeweed antiviral peptide, tricathecums, radioactive nuclides, and membrane-lytic enzymes. The antibody and the cytotoxin can be conjugated by chemical or by genetic engineering techniques.

D. Therapy with Bi-Specific Reagents

The antibodies of this invention can be used to target cytotoxic cells such as macrophages or cytotoxic T cells toward IgE-bearing B cells. The antibodies can be used to prepare bi-specific reagents having a specificity for a receptor of a cytotoxic cell and a specificity for IgE bearing B cells (but not basophils), as described in U.S. application Ser. No. 07/468,766.

E. Extracorporeal Treatment

While the antibodies of the invention can be used for in vivo application, they may also be used in extra-corporeal ex-vivo application, as described in U.S. application Ser. No. 07/468,766.

F. Other Immunoglobulin Isotypes

Antibody preparations specific for the membrane bound form of other immunoglobulin isotypes can be used, as described above, for diagnostic and therapeutic uses. For example, antibodies can be used to remove normal or tumorous B cells, for example, leukemic cells, bearing immunoglobulins of other isotypes (IgG, IgM and IgD) as well as IgE. Treatment of leukemia or other lymphoid tumors can be done in vivo or extracorporeally.

7. Anti-idionic Antibodies and Methods of Active Immunization Against Epitopes of the Invention The monoclonal antibodies of the invention can be used to generate parotopespecific, anti-idiotypic antibodies which offer another mode of treating IgE-mediated allergy, as described in U.S. application Ser. No. 07/468,766. These anti-idiotypic antibodies would have the uses described therein.

8. Peptide Analogues and Active Immunization Against the Epitopes of the Invention Even though the peptides of the invention probably are not immunogenic in humans, peptides with the same sequence and amino acid substitutions can be immunogenic and induce antibodies that cross react with the epitopes or these peptides. These peptide analogeus can be administered to patients suffering IgE-mediated allergies. The antibodies induced by this active immunization can achieve the same functions as the antibodies described above.

The invention is not limited to the terms, expressions, examples and emodiments set forth above, but is defined only in the claims which follow, and includes all equivalents of the subject matter of the claims.

What is claimed is:

1. An $\epsilon$ immunoglobulin transmembrane anchoring peptide resulting from the mRNA splicing of the C$\epsilon$4 exon, the $\epsilon$m1' exon, and the $\epsilon$m2 exon, or from the mRNA splicing of the C$\epsilon$4 exon and the $\epsilon$m2' exon.

2. A peptide segment of the following sequence: GLAGGSAQSQRAPDRVLCHSGQQQGL-PRAAGGSVPHPRCHCGAGRADWPGPP.

3. A peptide segment of the following sequence: GAAVPLSHAAGEAPDLPRLHQR-PPAPRLGRGHSRSTRPSFFSASA.

4. Human $\epsilon$ immunoglobulin containing the peptide segment of claim 2 or 3.

* * * * *